US012727777B2

(12) United States Patent
Chen et al.

(10) Patent No.: US 12,727,777 B2
(45) Date of Patent: Sep. 8, 2026

(54) CONTACTLESS ELECTROCARDIOGRAM MONITORING METHOD BASED ON MILLIMETER-WAVE RADAR

(71) Applicant: UNIVERSITY OF SCIENCE AND TECHNOLOGY OF CHINA, Hefei (CN)

(72) Inventors: Yan Chen, Hefei (CN); Jinbo Chen, Hefei (CN); Dongheng Zhang, Hefei (CN); Dong Zhang, Hefei (CN); Qibin Sun, Hefei (CN); Manqing Wu, Hefei (CN)

(73) Assignee: UNIVERSITY OF SCIENCE AND TECHNOLOGY OF CHINA, Hefei (CN)

( * ) Notice: Subject to any disclaimer, the term of this patent is extended or adjusted under 35 U.S.C. 154(b) by 217 days.

(21) Appl. No.: 18/713,327

(22) PCT Filed: Nov. 23, 2022

(86) PCT No.: PCT/CN2022/133773

§ 371 (c)(1),
(2) Date: May 24, 2024

(87) PCT Pub. No.: WO2023/093770

PCT Pub. Date: Jun. 1, 2023

(65) Prior Publication Data

US 2025/0017482 A1 Jan. 16, 2025

(30) Foreign Application Priority Data

Nov. 29, 2021 (CN) ......................... 202111454726.9

(51) Int. Cl.
*A61B 5/0507* (2021.01)
*A61B 5/318* (2021.01)

(52) U.S. Cl.
CPC ............ *A61B 5/0507* (2013.01); *A61B 5/318* (2021.01)

(58) Field of Classification Search
CPC ....... A61B 5/0507; A61B 5/318; A61B 5/346; A61B 5/7203; A61B 5/7225; A61B 5/7267; A61B 5/7264
See application file for complete search history.

(56) References Cited

U.S. PATENT DOCUMENTS 10,310,073 B1 * 6/2019 Santra .................. A61B 5/0816
11,278,241 B2 * 3/2022 Baheti .................... A61B 5/681
(Continued)

FOREIGN PATENT DOCUMENTS

CN 104274184 A 1/2015
CN 105476602 A 4/2016
(Continued)

OTHER PUBLICATIONS

Cardiopulmonary Activity Monitoring Using Millimeter Wave Radars (Year: 2020).*
(Continued)

*Primary Examiner* — Hien N Nguyen
(74) *Attorney, Agent, or Firm* — Myers Bigel, P.A.

(57) ABSTRACT

A contactless electrocardiogram monitoring method based on a millimeter wave radar is provided, including: step S1: transmitting a millimeter-wave signal to a target to be tested and receiving an echo signal using the millimeter-wave radar; step S2: performing a signal processing on the received echo signal to extract cardiac mechanical activity data hidden in the echo signal; step S3: constructing an end-to-end network architecture for the extracted cardiac mechanical activity data, so as to complete a cross-domain mapping from a cardiac mechanical activity to a cardiac electrical activity; and step S4: based on a deep learning
(Continued)

network architecture which has learned cross-domain mapping of the cardiac mechanical activity and the cardiac electrical activity, inputting cardiac mechanical activity data extracted at a current moment, and outputting an ECG measurement result for the current moment, so as to finally complete contactless electrocardiogram monitoring.

6 Claims, 5 Drawing Sheets

(56) References Cited

U.S. PATENT DOCUMENTS

| | | | | |
|---|---|---|---|---|
| 2008/0077015 | A1 * | 3/2008 | Boric-Lubecke | G01S 13/888 600/453 |
| 2011/0112425 | A1 | 5/2011 | Muhlsteff et al. | |
| 2011/0245690 | A1 * | 10/2011 | Watson | A61B 5/02416 600/509 |
| 2014/0343393 | A1 | 11/2014 | Lee et al. | |
| 2017/0150906 | A1 | 6/2017 | Roessler | |
| 2018/0279884 | A1 | 10/2018 | Ahmad et al. | |
| 2020/0386879 | A1 * | 12/2020 | Shouldice | A61B 5/0507 |
| 2021/0045656 | A1 * | 2/2021 | Rahman | A61B 7/003 |
| 2021/0093203 | A1 | 4/2021 | Zhong et al. | |
| 2024/0398259 | A1 * | 12/2024 | Shavit | G06F 21/32 |

FOREIGN PATENT DOCUMENTS

| | | | | |
|---|---|---|---|---|
| CN | 109965858 | A | 7/2019 | |
| CN | 110192850 | A | 9/2019 | |
| CN | 112401863 | A | 2/2021 | |
| CN | 112971771 | A | 6/2021 | |
| CN | 112986941 | A | 6/2021 | |
| CN | 113384250 | A | 9/2021 | |
| CN | 113420624 | A | 9/2021 | |
| CN | 114052740 | A | 2/2022 | |
| EP | 2368492 | A1 | 9/2011 | |
| JP | 2006304963 | A | 11/2006 | |
| JP | 2010061450 | A | 3/2010 | |
| JP | 2011050604 | A | 3/2011 | |
| JP | 2020181529 | A | 11/2020 | |
| JP | 2020192187 | A | 12/2020 | |
| WO | WO-2015174879 | A1 * | 11/2015 | A61B 5/0205 |
| WO | 2021204939 | A1 | 10/2021 | |

OTHER PUBLICATIONS

Supplementary European Search Report corresponding to European Application No. 22897853.2 (mailed Oct. 13, 2025).

Dell'Aversano et al., "Through the Wall Breathing Detection by Means of a Doppler Radar and MUSIC Algorithm", IEEE Sensors Letters 1(3):1-4, (May 16, 2017).

Toda et al., "ECG Signal Reconstruction using FMCW Radar and Convolutional Neural Network", IEEE 20th International Symposium on Communications and Information Technologies:176-181, (Oct. 19, 2021).

Wang et al., "1-D Microwave Imaging of Human Cardiac Motion: An Ab-initio Investigation", IEEE Transactions on Microwave Theory and Techniques 61(5):2101-2107, (Mar. 29, 2013).

Xu et al., "Cardiacwave: A mmWave-Dased Scheme of Non-contact and High-Definition Heart Activity Computing", Proceedings of the ACM on Interactive, Mobile, Wearable and Ubiquitous Technologies 5(3):1-26, (Sep. 14, 2021).

Yeh et al., "Fine Position Estimation of a Myocardium Phantom using a UWB Radar", 2019 IEEE Radar Conference:1-6, (Apr. 22, 2019).

Chinese Office Action corresponding to CN Application No. 202111454726.9 issued Jul. 13, 2022 (15 pages, including English translation).

International Search Report and Written Opinion corresponding to PCT/CN2022/133773, mailed Feb. 21, 2023 (11 pages, including English translation).

Chen, Jinbo , et al., "Contactless Electrocardiogram Monitoring with Millimeter Wave Radar", IEEE Transactions on Mobile Computing, vol. 23, No. 1, 2024, 270-285.

Konishi, Kentaro , et al., "Automatic Tracking of Human Body Using Millimeter-Wave Adaptive Array Radar for Noncontact Heart Rate Measurement", Proceedings of 2018 Asia-Pacific Microwave Conference, 2018, 836-838.

Office Action issued in corresponding Japanese Application No. 2024-531547, dated Mar. 5, 2025.

* cited by examiner

CONTACTLESS ELECTROCARDIOGRAM MONITORING METHOD BASED ON MILLIMETER-WAVE RADAR

CROSS-REFERENCE TO RELATED APPLICATION(S)

This application is a Section 371 National Stage Application of International Application No. PCT/CN2022/133773, filed on Nov. 23, 2022, entitled "CONTACTLESS ELECTROCARDIOGRAM MONITORING METHOD BASED ON MILLIMETER-WAVE RADAR", which claims priority to Chinese Application No. 202111454726.9, filed on Nov. 29, 2021, the contents of which are incorporated herein by reference in their entireties.

TECHNICAL FIELD

The present disclosure relates to the field of intelligent sensing technology, and in particular to a contactless electrocardiogram monitoring method based on a millimeter-wave radar.

BACKGROUND

Electrocardiogram (ECG) is currently one of the most important biomedical signals used to depict cardiac activity to provide basic information for the diagnosis of heart disease. Experimental evidence shows that diagnosis, control and prevention based on continuous monitoring and analysis may significantly reduce the incidence and harm of heart disease. In current ECG monitoring methods, tiny potential changes in different parts of the body caused by the electrical activity generated by the contraction of cardiac muscle are detected based on electrodes attached to human skin. Although the electrode-based ECG monitoring has been widely used in clinical diagnosis and daily prevention, the requirements of contact with human body during the measurement process still impose many limitations on practical use. For example, the foreign body sensation caused by the long-term attachment of electrodes to the skin makes patients much subjectively resistant to long-term continuous monitoring, and for some patients with burns and infectious diseases, and infants, it is difficult to achieve the attachment of the electrodes to the skin.

A process of cardiac activity is completed based on the functional cardiac mechanical movement, and cardiac mechanical activity itself will also cause changes in the cardiac electrical activity. Theoretically, the cardiac mechanical activity and the cardiac electrical activity are mappings of homologous information in different domains. With the development of millimeter-wave radars, the increasingly accurate spatial perception capability enables the millimeter-wave radars to provide possibility for accurate contactless monitoring of the cardiac mechanical activity. However, the reflection of the electromagnetic waves on the human body is very complex and susceptible to interference. Also, the mechanical movement caused by the cardiac activity itself has a very small amplitude (usually considered to be in a range of 0.2 mm to 0.5 mm), which is often submerged in other body movements with larger amplitudes (such as breathing). Existing methods mainly focus on performing coarse-grained monitoring on cardiac activity, such as estimation of human heart rate, thus the current methods have very limited performance and fail to achieve accurate measurement of the cardiac mechanical activity.

SUMMARY

The present disclosure provides a contactless electrocardiogram monitoring method based on a millimeter wave radar, including step S1 to step S3:

step S1: transmitting a millimeter-wave signal to a target to be tested and receiving an echo signal using the millimeter-wave radar; step S2: performing a signal processing on the received echo signal to extract cardiac mechanical activity data hidden in the echo signal; and step S3: constructing an end-to-end network architecture for the extracted cardiac mechanical activity data, so as to complete a cross-domain mapping from a cardiac mechanical activity to a cardiac electrical activity According to the embodiments of the present disclosure, step S2 includes sub-steps S21 to S25.

In sub-step S21, a virtual antenna array is constructed based on a physical arrangement of antennas of the millimeter-wave radar, a phase shift vector is constructed based on an antenna spacing and a signal bandwidth in the virtual antenna array, and a calculation is made for a spatial beamforming, so as to complete a spatial filtering of the echo signal of the radar. In sub-step S22, phases are extracted from signals at all the spatial positions after the spatial filtering, and micro-motion signals are extracted from the phases. In sub-step S23, the micro-motion signals are evaluated for a correlation to a cardiac micro-motion every periodic time T based on a periodic template matching, so as to determine a spatial position related to the cardiac micro-motion. In sub-step S24, a threshold filtering is performed on the evaluated micro-motion signals, to retain micro-motion signals exceeding a threshold, and eliminate other micro-motion signals. In sub-step S25, the cardiac mechanical activity data is extracted from the retained micro-motion signals, so as to complete measurement of the cardiac mechanical activity by the millimeter-wave radar.

According to the embodiments of the present disclosure, a Lanczos differential filter based on minimum variance smoothing is used to extract the micro-motion signals from the phases.

According to the embodiments of the present disclosure, a spatial coherence filtering based on K-means clustering is performed on the retained micro-motion signals to extract the cardiac mechanical activity data.

According to the embodiments of the present disclosure, step S3 includes sub-steps S31 to S33.

In sub-step S31, a convolutional neural network is used to extract a time-domain feature of the cardiac micro-motion data. In sub-step S32, a position encoding is performed on a spatially sparse time-domain feature and a Transformer module with a multi-head attention mechanism is used to extract a spatial-domain feature of the cardiac micro-motion data. In sub-step S33, an element-wise multiplication is performed on the time-domain feature and the spatial-domain feature of the cardiac micro-motion to complete fusion and extraction of a deep feature of the cardiac activity.

According to the embodiments of the present disclosure, step S3 further includes sub-step S34, in which the cardiac activity is modeled as a time autoregressive model:

$$p(X \mid h) = \prod_{t=1}^{T} p(x_t \mid x_1, \ldots , x_{t-1}, h_t),$$

where an ECG measurement result $x_t$ at each moment is a conditional probability distribution of ECG measurement results ($x_1, \ldots, x_{t-1}$) at historical time and the deep feature $h_t$ of the cardiac activity at a current moment.

According to the embodiments of the present disclosure, a temporal convolutional network is used to construct a sequence-to-sequence decoder model, and dilated convolution characteristics in the temporal convolutional network are used to achieve a long-term memory of the decoder model on high-sampling-rate radar data.

According to the embodiments of the present disclosure, step S3 further includes sub-step S35: for an ECG prediction result and a real ECG measurement result at each moment, using a loss function based on L2 distance to learn a mapping relationship between different domains, so as to enable a deep learning network architecture to calculate a cross-domain mapping relationship between the cardiac mechanical activity and the cardiac electrical activity after training the deep learning network architecture with a large amount of data.

According to the embodiments of the present disclosure, the contactless electrocardiogram monitoring method based on the millimeter-wave radar according to claim 1, further includes step S4: based on a deep learning network architecture which has learned cross-domain mapping of the cardiac mechanical activity and the cardiac electrical activity, inputting cardiac mechanical activity data extracted at a current moment, and outputting an ECG measurement result for the current moment, so as to finally complete contactless electrocardiogram monitoring.

The present disclosure provides a contactless electrocardiogram monitoring method based on a millimeter-wave radar, which may achieve stable, effective and accurate measurement of the mechanical activity of human heart, and may achieve cross-domain information mapping from cardiac mechanical activity to cardiac electrical activity. The measurement is a contactless measurement, which is safer and more convenient. The inconvenience and shortcomings caused by the fact that the ECG monitoring in the prior art is based on the contact measurement methods may be mitigated, and technical problems such as that the existing contactless heart measurement technology may only perform coarse-grained monitoring on the cardiac activity of human body (such as heart rate, heartbeat interval, etc.) may be solved.

DETAILED DESCRIPTION OF EMBODIMENTS

The present disclosure provides a contactless electrocardiogram monitoring method based on a millimeter-wave radar, which combines the millimeter-wave radar with deep learning so as to build a bridge for contactless electrocardiogram monitoring. The core of the technology is how to use the millimeter-wave radar to achieve stable, effective and accurate measurement of the mechanical activity of the human heart and how to design a deep learning network structure based on the sensing data of the radar and the characteristics of the cardiac activity to mine a deep feature and achieve cross-domain information mapping, so as to finally convert a radar observation representation of the cardiac mechanical activity to an electrocardiogram representation of the cardiac electrical activity. Existing methods have not yet designed and implemented an end-to-end cross-domain learning architecture for the cardiac activity based on the characteristics of millimeter-wave radar data and complex physiological states of the heart.

In order to make the objectives, technical solutions and advantages of the present disclosure more clear, the present disclosure will be further described in detail below in conjunction with specific embodiments and with reference to the accompanying drawings.

Figure 1:
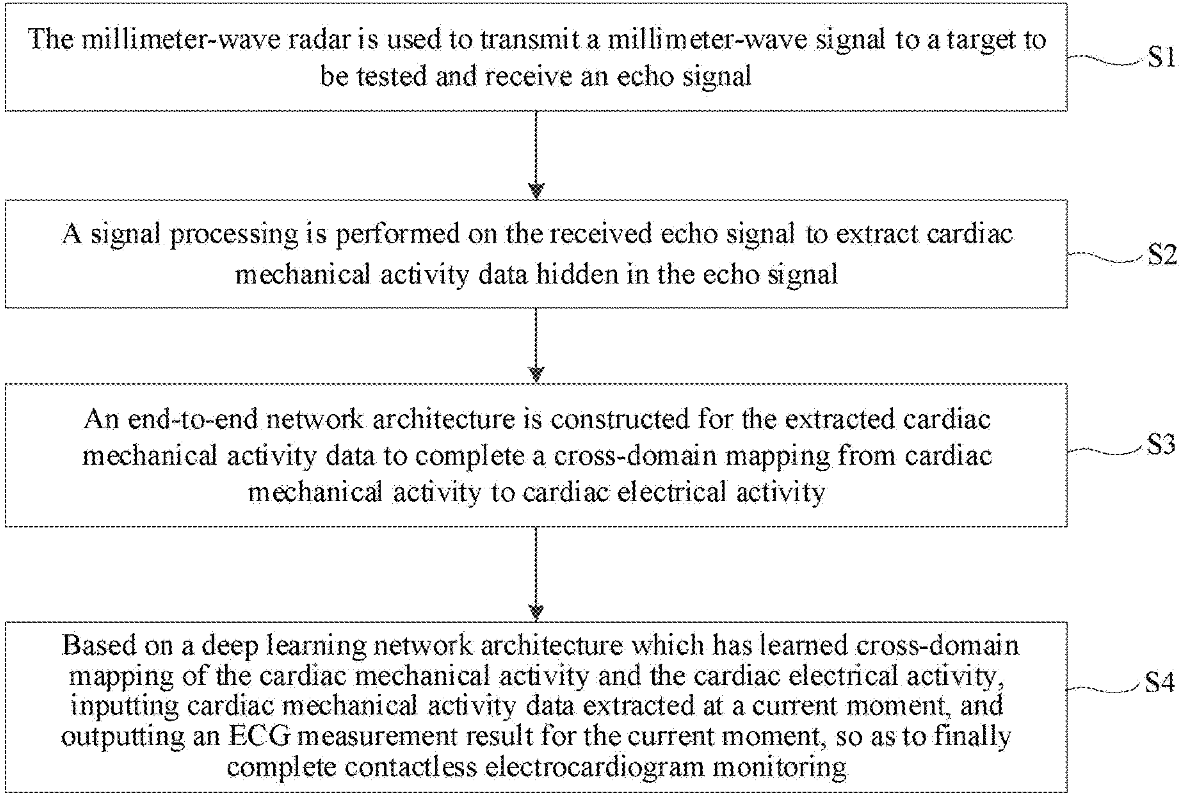
FIG. 1 shows a schematic flowchart of a contactless electrocardiogram monitoring method based on a millimeter-wave radar according to an embodiment of the present disclosure.
Figure 7:
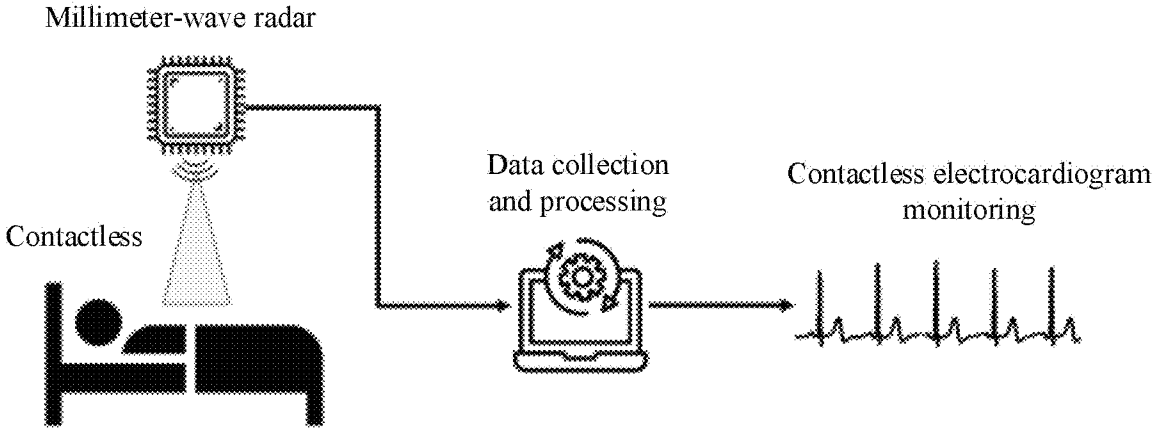
FIG. 7 shows a schematic diagrams of a working principle and an architecture of contactless electrocardiogram monitoring based on a millimeter-wave radar according to an embodiment of the present disclosure.

In the embodiments of the present disclosure, a contactless electrocardiogram monitoring method based on a millimeter-wave radar is provided. As shown in FIGS. 1 and 7, the contactless electrocardiogram monitoring method based on the millimeter-wave radar includes the following steps.

In step S1, the millimeter-wave radar is used to transmit a millimeter-wave signal to a target to be tested and receive an echo signal.

In step S2, a signal processing is performed on the received echo signal to extract cardiac mechanical activity data hidden in the echo signal.

In step S3, an end-to-end network architecture is constructed for the extracted cardiac mechanical activity data to complete a cross-domain mapping from cardiac mechanical activity to cardiac electrical activity.

According to the embodiments of the present disclosure, the target to be tested is a human or other animals.

In the embodiments of the present disclosure, step S2 includes sub-step S21 to sub-step S25.

Figure 2:
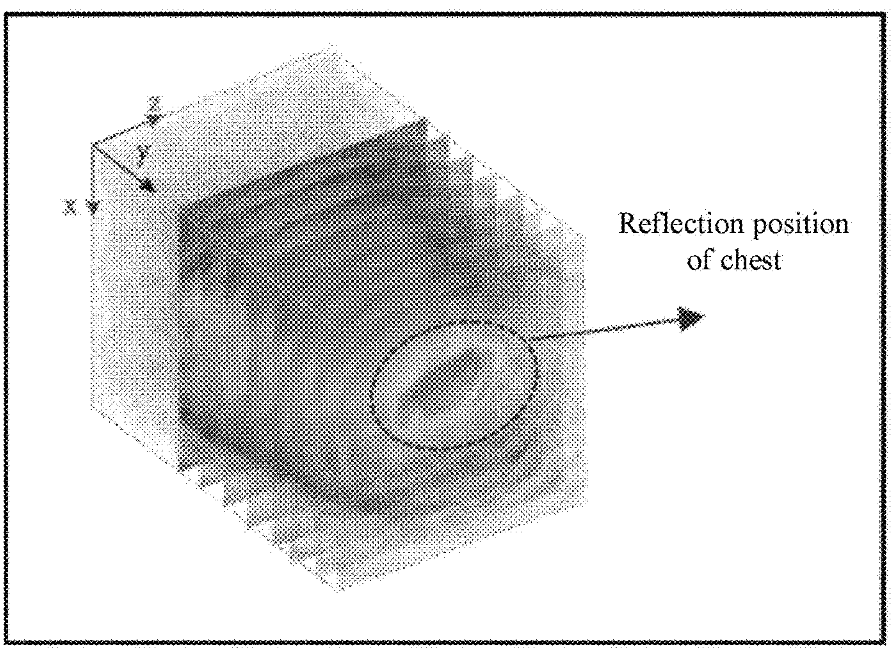
FIG. 2 shows a schematic diagram of a result of spatial beamforming during a contactless electrocardiogram monitoring process according to an embodiment of the present disclosure.

In sub-step S21, a virtual antenna array is constructed based on a physical arrangement of antennas of the millimeter-wave radar, a phase shift vector is constructed based on an antenna spacing and a signal bandwidth in the virtual antenna array, and a calculation is made for a spatial beamforming, so as to complete a spatial-domain filtering of the echo signal of the radar. The result is as shown in FIG. 2. It will be seen from the figure that after the spatial filtering is performed on the signal received by the radar, signal reflections at different spatial positions are successfully separated.

Figure 3:
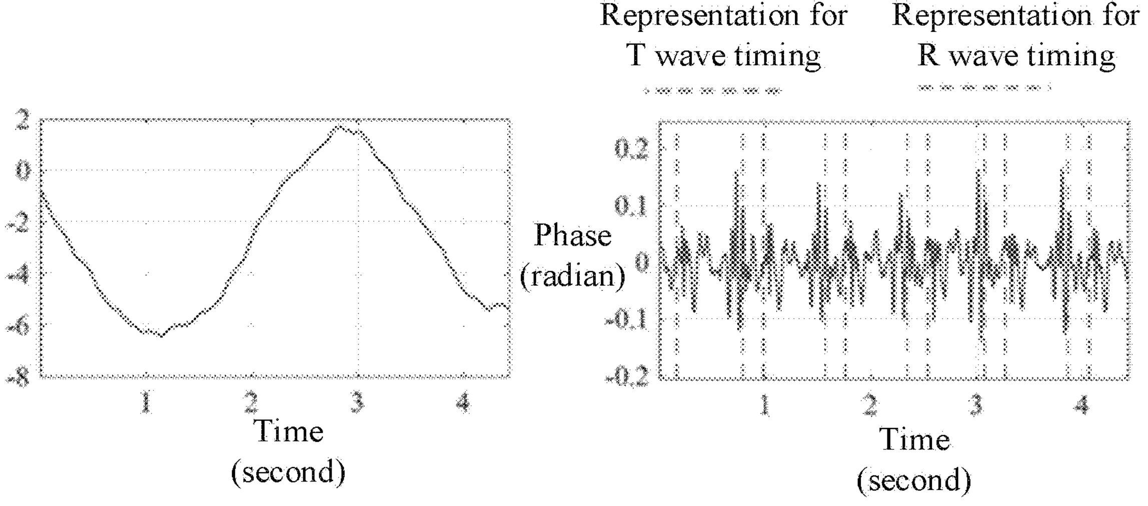
FIG. 3 shows schematic diagrams of a phase of a signal near human chest and a filtered micro-motion signal according to an embodiment of the present disclosure.

In sub-step S22, phases are extracted from signals at all the spatial positions after the spatial filtering, and micro-motion signals are extracted from the phases. The result is as shown in FIG. 3. The phase information near the chest shows that a main motion trend at this time comes from human respiratory activity, which has a larger amplitude.

In sub-step S23, the micro-motion signals are evaluated for a correlation to a cardiac micro-motion every periodic time T based on a periodic template matching, so as to determine a spatial position related to the cardiac micro-motion.

Figure 4:
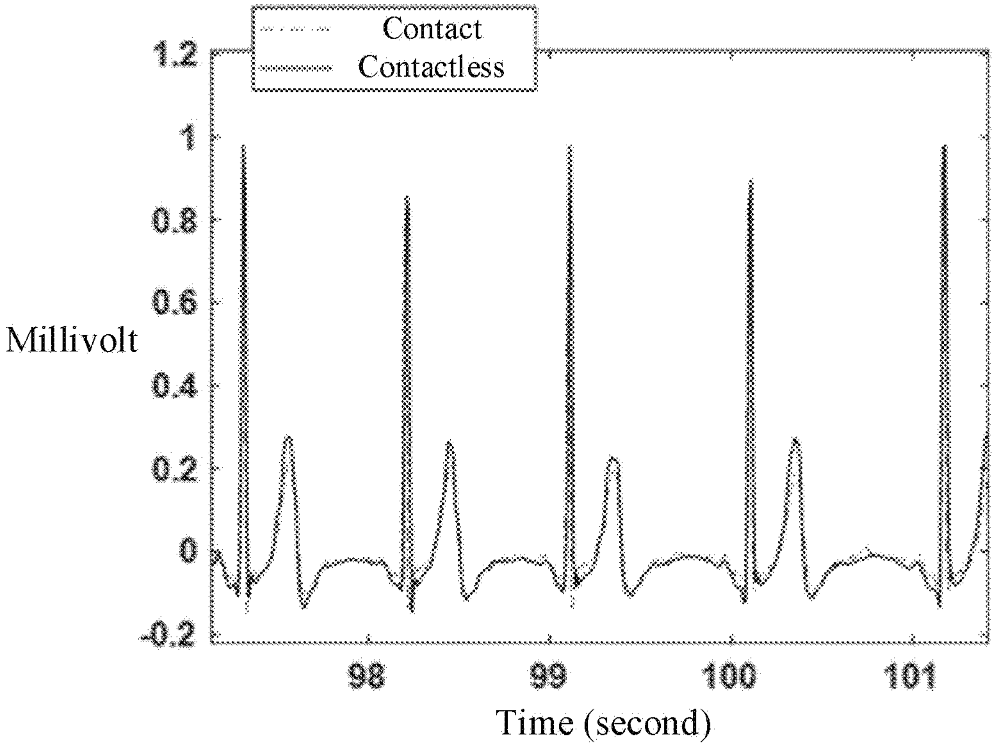
FIG. 4 shows a schematic diagram of comparison between a result of a contactless electrocardiogram monitoring and a result of a contact electrocardiogram monitoring simultaneously performed, according to an embodiment of the present disclosure.

In sub-step S24, a threshold filtering is performed on the evaluated micro-motion signals, to retain micro-motion signals exceeding the threshold and eliminate other micro-motion signals. As shown in FIG. 4, the micro-motion signals exceeding the threshold may eliminate interference by the motion with a large amplitude. R wave peak and T wave peak of the electrocardiogram of a corresponding time are compared. It will be seen that the micro-motion signal has the same periodicity as the cardiac activity.

In sub-step S25, the cardiac mechanical activity data is extracted from the retained micro-motion signals, so as to complete measurement of the cardiac mechanical activity by the millimeter-wave radar.

More specifically, the virtual antenna array is constructed based on the physical arrangement of the antennas of the millimeter-wave radar, the phase shift vector is constructed based on the antenna spacing and the signal bandwidth in the virtual antenna array, and the calculation is made for the spatial beamforming, so as to complete the spatial filtering of the echo signal of the radar. A signal S(x,y,z,t) at a spatial position (x,y,z) at time t may be represented as:

$$S(x, y, z, t) = \sum_{m=1}^{M}\sum_{n=1}^{N}\sum_{t=1}^{T} y_{n,m,t} e^{j2\pi \frac{kr(x,y,z,n,m)}{c} t} e^{j2\pi \frac{r(x,y,z,n,m)}{\lambda}}$$

Here, N is the number of receiving antennas, M is the number of transmitting antennas, $y_{n,m,t}$ is a signal received by a channel defined by an $n^{th}$ receiving antenna and an $m^{th}$ transmitting antenna at time t, k represents a variation rate of an emission frequency, λ represents a wavelength of the emitted signal, r(x,y,z,n,m) represents a round-trip distance from the $m^{th}$ transmitting antenna to a target location (x,y,z) and back to the $n^{th}$ receiving antenna, and c is the speed of light.

The phases are extracted from the signals at all spatial positions after the spatial filtering, and a Lanczos differential filter based on minimum variance smoothing is used to extract the micro-motion signals from the phases.

The micro-motion signals are evaluated for the correlation to the cardiac micro-motion every periodic time T based on the periodic template matching, so as to determine the spatial position related to the cardiac micro-motion. Then, the threshold filtering is performed on the evaluated micro-motion signals, to retain the micro-motion signals exceeding the threshold and eliminate the other micro-motion signals. A spatial coherence filtering based on K-means clustering is performed on the retained micro-motion signals to extract the cardiac mechanical activity data, so as to finally complete the measurement of the cardiac mechanical activity by the millimeter-wave radar.

In the embodiments of the present disclosure, step S3 includes sub-step S31 to sub-step S33.

In sub-step S31, a convolutional neural network is used to extract a time-domain feature of the cardiac micro-motion data.

In sub-step S32, a position encoding is performed on a spatially sparse time-domain feature and a Transformer module with a multi-head attention mechanism is used to extract a spatial-domain feature of the cardiac micro-motion data.

In sub-step S33, an element-wise multiplication is used for the time-domain feature and the spatial-domain feature of the cardiac micro-motion to complete fusion and extraction of a deep feature of the cardiac activity.

More specifically, for the temporal and spatial characteristics in the cardiac mechanical activity data, first, the convolutional neural network is used to extract the time-domain feature of the cardiac micro-motion data, then the position encoding is performed on the spatially sparse time-domain feature, and the Transformer module with the multi-head attention mechanism is used to extract the spatial-domain feature of the cardiac micro-motion data. Then, element-wise multiplication is used on the time-domain feature and the spatial-domain feature of the cardiac micro-motion, so as to complete the fusion and extraction of the deep feature of the cardiac activity.

According to the embodiments of the present disclosure, step S3 further includes sub-step S34, in which the cardiac activity is modeled as a time autoregressive model:

$$p(X \mid h) = \prod_{t=1}^{T} p(x_t \mid x_1, \ldots, x_{t-1}, h_t)$$

The ECG measurement result $x_t$ at each moment is a conditional probability distribution of the ECG measurement results $(x_1, \ldots, x_{t-1})$ at historical time and the deep feature $h_t$ of the cardiac activity at the current moment. The temporal convolutional network is used to construct a sequence-to-sequence decoder model, and dilated convolution characteristics in the temporal convolutional network are used to achieve a long-term memory of the decoder model on high-sampling-rate radar data.

According to the embodiments of the present disclosure, step S3 further includes sub-step S35, in which a loss function based on L2 distance is used for an ECG prediction result and a real ECG measurement result (contact measurement) at each moment to learn the mapping relationship between different domains, and after trained with a large amount of data, the deep learning network architecture may calculate the cross-domain mapping relationship between the cardiac mechanical activity and cardiac electrical activity.

In the embodiments of the present disclosure, as shown in FIG. 1, the contactless electrocardiogram monitoring method based on the millimeter-wave radar further includes step S4, in which based on the deep learning network architecture that is trained and completes the cross-domain mapping of the cardiac mechanical activity and the cardiac electrical activity, the cardiac mechanical activity data extracted at the current moment is input, and the ECG measurement result for the current moment is output, so as to finally complete the contactless electrocardiogram monitoring.

Figure 5:
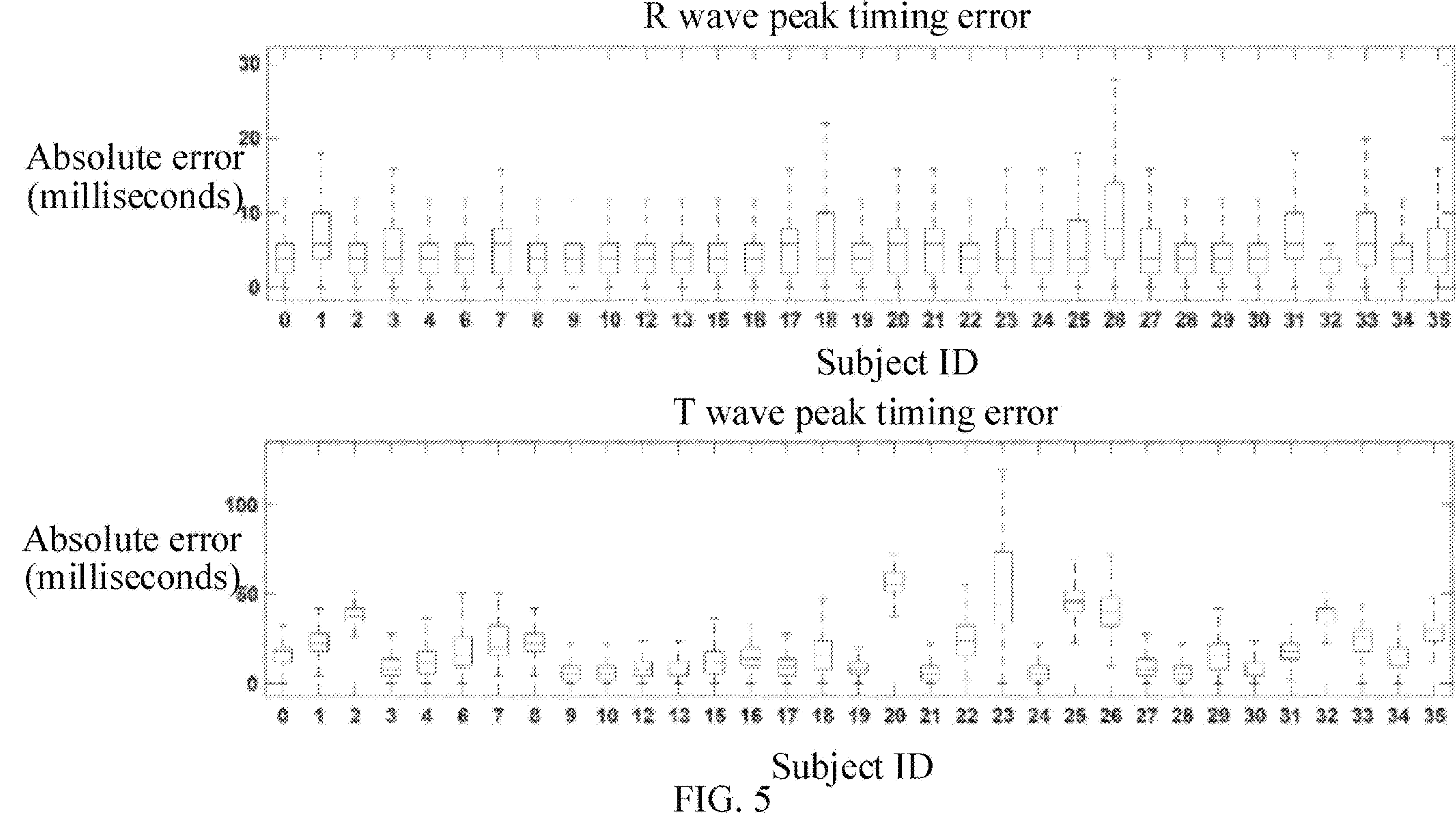
FIG. 5 shows schematic diagrams of determination performance of reference time points in contactless electrocardiogram monitoring results of 36 testers according to an embodiment of the present disclosure (R wave and T wave peak time).
Figure 6:
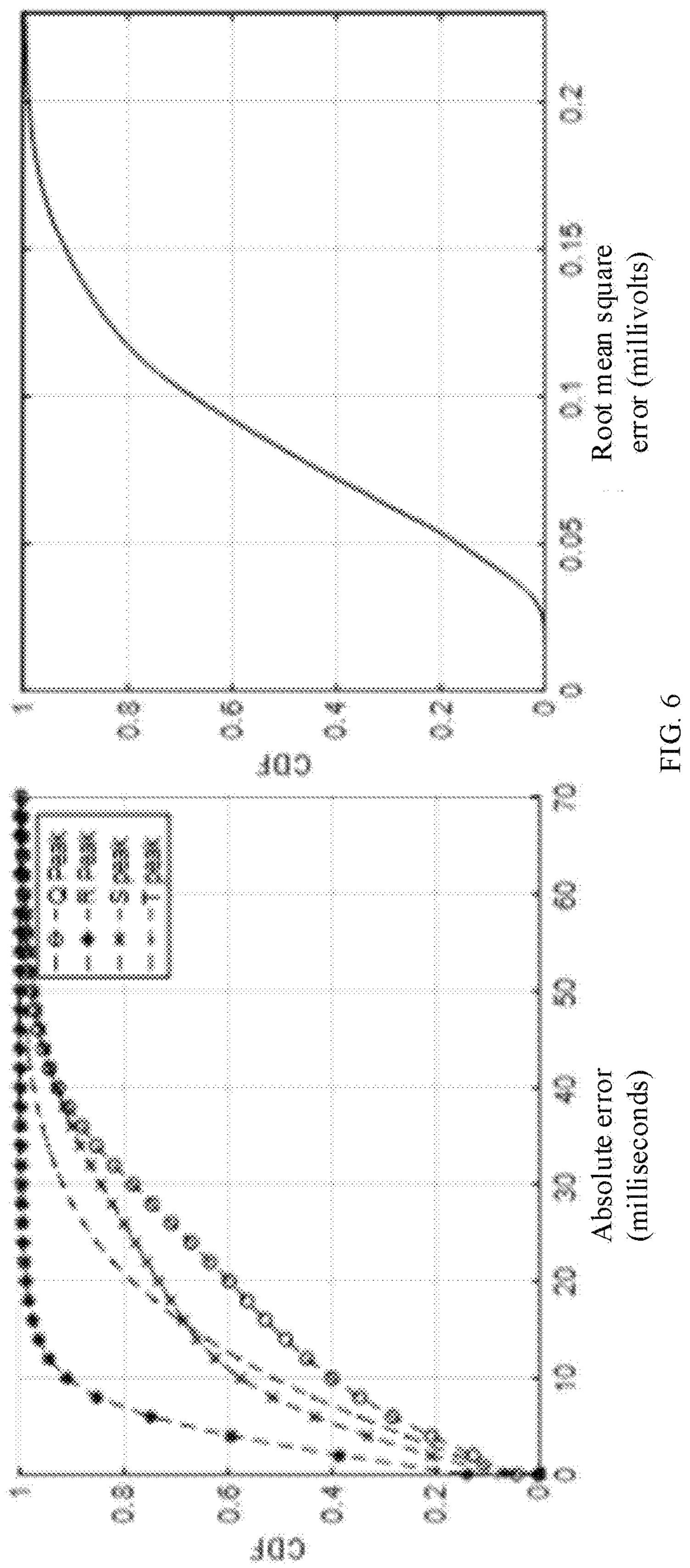
FIG. 6 shows schematic diagrams of cumulative statistical results of a time error and an amplitude root-mean-square error of contactless electrocardiogram monitoring of 36 testers according to an embodiment of the present disclosure (Q Peak: Q wave peak; R Peak: R wave peak; S Peak: S wave peak; and T peak: T wave peak).

In the embodiments of the present disclosure, when the performance of the contactless electrocardiogram monitoring is verified using the algorithm proposed in the present disclosure, the target to be tested keeps lying on the bed and the radar is 0.5 m apart therefrom (as shown in FIG. 7). During the test, the radar is in a working mode of 3 transmitters and 4 receivers, a starting frequency of the signal is set to 78 Ghz, a bandwidth is 4 Ghz, a Chirp interval is 45 us, a frame rate is 200 Hz, and the number of sampling points is 256. A total of 36 people are tested, and the radar data and its paired contact electrocardiogram monitoring data within 3 minutes are collected each time, for a total of about 810 minutes. Analysis of the performance of the contactless ECG monitoring is as shown in FIGS. 5 and 6.

The embodiments of the present disclosure have been described in detail with reference to the accompanying drawings. It should be noted that implementations not shown or described in the drawings or the specification are all in forms known to those of ordinary skill in the art and thus are not described in detail. In addition, the above definitions of each element and method are not limited to the various specific structures, shapes or methods mentioned in the embodiments, which may be simply modified or replaced by those of ordinary skill in the art.

Based on the above descriptions, those skilled in the art will have a clear understanding of the contactless electrocardiogram monitoring method based on the millimeter-wave radar according to the present disclosure.

In summary, the present disclosure provides a contactless electrocardiogram monitoring method based on a millimeter-wave radar, which is a contactless electrocardiogram monitoring method of cardiac mechanical activity measurement and cardiac electrical activity cross-domain deep learning based on the millimeter-wave radar. The combination of the millimeter-wave radar and deep learning builds a bridge for the contactless ECG monitoring, the millimeter-wave radar is used to achieve stable, effective and accurate measurement on mechanical activity of human heart and a deep learning network structure is designed for the radar sensing data and the characteristics of cardiac activity to mine deep features and achieve cross-domain information mapping, and finally convert the radar observation representation of the cardiac mechanical activity to the electrocardiogram representation of cardiac electrical activity.

The above-mentioned specific embodiments of the present disclosure do not constitute a limitation on the scope of the present disclosure. Any other corresponding changes and deformations made based on the technical concept of the present disclosure shall be included in the protection scope of the claims of the present disclosure.

What is claimed is:

1. A contactless electrocardiogram monitoring method based on a millimeter-wave radar, comprising:

step S1: transmitting a millimeter-wave signal to a target to be tested and receiving an echo signal using the millimeter-wave radar;

step S2: performing a signal processing on the received echo signal to extract cardiac mechanical activity data hidden in the echo signal; and step S3: constructing an end-to-end network architecture for the extracted cardiac mechanical activity data, so as to complete a cross-domain mapping from a cardiac mechanical activity to a cardiac electrical activity; and step S4: based on a deep learning network architecture which has learned the cross-domain mapping from the cardiac mechanical activity to the cardiac electrical activity, inputting the cardiac mechanical activity data extracted at a current moment, and outputting an ECG measurement result for the current moment, so as to finally complete a contactless electrocardiogram monitoring, wherein the step S2 comprises:

sub-step S21: constructing a virtual antenna array based on a physical arrangement of antennas of the millimeter-wave radar, constructing a phase shift vector based on an antenna spacing and a signal bandwidth in the virtual antenna array, and making a calculation for a spatial beamforming, so as to complete a spatial-domain filtering of the echo signal of the millimeter-wave radar;

sub-step S22: extracting phases from signals at all spatial positions after the spatial-domain filtering, and extracting micro-motion signals from the phases;

sub-step S23: evaluating the micro-motion signals for a correlation to a cardiac micro-motion every periodic time T based on a periodic template matching, so as to determine a spatial position related to the cardiac micro-motion;

sub-step S24: performing a threshold filtering on the evaluated micro-motion signals, to retain micro-motion signals exceeding a threshold and eliminate other micro-motion signals; and sub-step S25: extracting the cardiac mechanical activity data from the micro-motion signals that were retained, so as to complete a measurement of the cardiac mechanical activity by the millimeter-wave radar, wherein the step S3 comprises:

sub-step S31: extracting a time-domain feature of cardiac micro-motion data using a convolutional neural network;

sub-step S32: performing a position encoding on a spatially sparse time-domain feature, and extracting a spatial-domain feature of the cardiac micro-motion data using a Transformer module with a multi-head attention mechanism; and sub-step S33: performing an element-wise multiplication on the time-domain feature and the spatial-domain feature of the cardiac micro-motion data, so as to complete fusion and extraction of a deep feature of a cardiac activity.

2. The contactless electrocardiogram monitoring method based on the millimeter-wave radar according to claim 1, wherein a Lanczos differential filter based on minimum variance smoothing is used to extract the micro-motion signals from the phases.

3. The contactless electrocardiogram monitoring method based on the millimeter-wave radar according to claim 1, wherein a spatial coherence filtering based on K-means clustering is performed on the micro-motion signals that were retained to extract the cardiac mechanical activity data.

4. The contactless electrocardiogram monitoring method based on the millimeter-wave radar according to claim 1, wherein the step S3 further comprises:

sub-step S34: modeling the cardiac activity as a time autoregressive model:

$$p(X|h)=\prod_{t=1}^{T}p(x_t|x_1, \ldots, x_{t-1}, h_t),$$

wherein an ECG measurement result $x_t$ at each moment is a conditional probability distribution of ECG measurement results $(x_1, \ldots x_{t-1})$ at historical time and the deep feature, $h_t$, of the cardiac activity at the current moment.

5. The contactless electrocardiogram monitoring method based on the millimeter-wave radar according to claim 1, wherein a temporal convolutional network is used to construct a sequence-to-sequence decoder model, and dilated convolution characteristics in the temporal convolutional network are used to achieve a long-term memory of the sequence-to-sequence decoder model on high-sampling-rate radar data.

6. The contactless electrocardiogram monitoring method based on the millimeter-wave radar according to claim 1, wherein the step S3 further comprises:

sub-step S35: for an ECG prediction result and a real ECG measurement result at each moment, using a loss function based on L2 distance to learn a mapping relationship between different domains, so as to enable the deep learning network architecture to calculate a cross-domain mapping relationship between the cardiac mechanical activity and the cardiac electrical activity after training the deep learning network architecture with a large amount of data.

* * * * *